(12) United States Patent
Gharib (10) Patent No.: US 8,235,944 B2
(45) Date of Patent: Aug. 7, 2012

(54) MEDICAL DEVICE FOR PLACEMENT OF CONTINUOUS REGIONAL ANESTHESIA CATHETERS

(76) Inventor: Morteza Gharib, Hollidaysburg, PA (US)

( * ) Notice: Subject to any disclaimer, the term of this patent is extended or adjusted under 35 U.S.C. 154(b) by 309 days.

(21) Appl. No.: 12/700,529

(22) Filed: Feb. 4, 2010

(65) Prior Publication Data
US 2010/0210997 A1    Aug. 19, 2010

Related U.S. Application Data

(60) Provisional application No. 61/153,277, filed on Feb. 17, 2009.

(51) Int. Cl.
*A61M 5/178* (2006.01)
(52) U.S. Cl. .......... 604/158; 604/21; 604/117; 604/162; 604/163; 604/528
(58) Field of Classification Search .............. 604/21, 604/117, 158, 162, 163, 164.01, 170.01–170.03, 604/171–172, 192, 198, 528
See application file for complete search history.

(56) References Cited

U.S. PATENT DOCUMENTS

| | | | | | |
|---|---|---|---|---|---|
| 3,572,334 | A | * | 3/1971 | Petterson | 604/159 |
| 3,595,230 | A | * | 7/1971 | Suyeoka et al. | 604/192 |
| 5,007,901 | A | * | 4/1991 | Shields | 604/110 |
| 6,298,256 | B1 | * | 10/2001 | Meyer | 600/373 |

* cited by examiner

*Primary Examiner* — Theodore Stigell (57) ABSTRACT

A medical device for placement of regional anesthesia catheters. The device comprises a hollow shaft needle, a plunger attached to the posterior end of the needle, a housing dimensioned so that plunger can slide inside the housing with friction, a regional anesthesia catheter preloaded inside the needle, a protective cover sheath covering the catheter, and a catheter adaptor attached to posterior end of the sheath and the catheter. The medical device allows a practitioner to quickly and effectively place a regional anesthesia catheter inside an organism without the use of an assistant, and with minimal risk of contaminating the catheter before it enters the organism's body. At the end, the needle is withdrawn inside the housing and disposed.

31 Claims, 8 Drawing Sheets

Prior Art

Fig. 4A

Prior Art

Fig. 4B

Prior Art

MEDICAL DEVICE FOR PLACEMENT OF CONTINUOUS REGIONAL ANESTHESIA CATHETERS

CROSS-REFERENCE TO RELATED APPLICATIONS

This application claims the benefit, under 35 U.S.C §119(e)(1), of U.S. provisional patent application No. 61/153,277 filed on Feb. 17, 2009, titled: "Medical Device for Placement of Continuous Regional Anesthesia Catheters," the disclosure of which is herein incorporated by reference.

STATEMENT REGARDING FEDERALLY SPONSORED RESEARCH

Not Applicable.

FIELD OF INVENTION

The invention relates generally to medical devices that enable the placement of catheters into body of an organism, and more specifically to medical devices designed to assist the placement of regional anesthesia catheters for continuous infusion of local anesthetics.

BACKGROUND

Regional anesthesia catheters are hollow body flexible catheters that are designed to be placed next to a nerve or nerve plexus of the human body, and kept in place for up to a few days. Liquid medicine is injected into proximal end of the catheter. The medication then exits from distal end of the catheter and is deposited around the nerve that is intended to be anesthetized. The dispersal of medication around the nerve causes the area innervated by that nerve to become anesthetized. In current anesthesia practice, hollow shaft metal needles are used to place such catheters into position.

Such needles are covered with an electrically insulating covering over the outer surface of most of their length, except the tip and proximal end. An electric impulse sent to the needle is conveyed axially down to the tip of the needle and not radially to surrounding tissues. This allows for more precise placement of the needle tip. A stimulating wire is attached to the proximal end of the needle and is used to connect the needle to an electric supply source or so-called a nerve stimulator device. The distal end of the needle is placed through the skin of the patient and is advanced toward the target nerve. The amount of electric impulse that is sent toward the needle tip is gradually decreased as the needle advances into the patient's body, which helps to localize the target nerve. A muscle contraction at a specific low current verifies the proximity of the needle tip to that nerve. Next, the catheter is placed through needle.

Needles and catheters come in different gauges and lengths, and it is imperative to use catheters with matching needles. Catheters are either stimulating or non-stimulating. Non-stimulating catheters are composed of an elongated hollow body and generally are similar to epidural catheters. Stimulating catheters generally have a hollow body and means for conveying electric current from the proximal end of the catheter to its distal tip. Only a small portion of the distal and proximal ends of the catheter are electrically exposed, while the body is electrically nonconductive. This allows for precise placement of catheter tip next to a nerve.

These days some practitioners use ultrasound devices to visualize the target nerve and place the needle tip, followed by the catheter tip, next to the target nerve. Practitioners may choose to perform the procedure, using ultrasound alone, or they may employ ultrasound and a nerve stimulator simultaneously. In current practice, however, the majority of practitioners prefer to use nerve stimulators.

Placement of regional anesthesia catheters is done using strict sterile techniques to avoid catheter and needle contamination, and thus patient infection. For example, the skin area were where the needle and catheter will be inserted into the patient is prepped and extensively draped. The long resilient catheter is always prone to contamination from surrounding objects. It is also necessary for the practitioner to wear a mask, hat and sterile gloves and even sterile gown in some instances. An assistant is needed to help open sterile packages, connect and disconnect stimulating wires of needle and catheter to nerve stimulator, and operate the nerve stimulator. The assistant will help utilize the ultrasound device as well, if one is used.

SUMMARY

The current invention is directed to a device that:
Reduces chance and frequency of catheter and needle contamination.
Reduces time needed to place the catheter adjacent to the target nerve.
Eliminates need for an assistant in most parts of a procedure.
Eliminates the need for anesthesia provider to wear hat, mask, sterile gloves, and gown.
Eliminates the need to drape insertion site.
Reduces risk of needle injury to medical staff because the needle is housed safely in a protective covering.

In this invention, a metal hollow shaft needle is manufactured to a size that is almost twice as long as commercially-available similar needles. The needle is electrically insulated throughout most of its length, on the outer surface, except its proximal end and distal tip. The needle's proximal end may be attached to a stimulating wire which is adapted to allow it to be connected to a nerve stimulator device. The proximal portion of the needle shaft is permanently placed inside a plunger and the plunger is placed inside a housing. The plunger is situated inside the housing so that it can slide up and down the housing with friction. A removable protective cap is placed over distal end of the housing to ensure sterility.

In the present invention, a stimulating regional anesthesia catheter is preloaded inside the needle. The catheter tip may be electrically in touch with electrically conductive inside surface of the needle. A protective sheath made of clear collapsible plastic covers most of the length of the catheter, which is left proximal to the needle. The sheath has a proximal hub and a distal hub and is secured and sealed at the peripheral ends of the hubs. The distal hub is attached to the proximal end of the needle, while the proximal hub is placed around the proximal end of catheter, leaving a small portion of the catheter (approx. 1-2 cm.) out. A regional anesthesia catheter adaptor is attached to the sheath's proximal hub in a releasable manner. This adaptor accepts and rigidly maintains the catheter's proximal end. It has components to electrically connect the nerve stimulator to the catheter's proximal end and provides fluid access into the interior lumen of the catheter for injection of liquid medicine using a syringe or infusion pump.

After prepping the insertion site, the catheter adaptor is connected to a nerve stimulator device. The housing distal protective cap is removed and the distal end of the housing is placed over the insertion site. The needle is then advanced toward the target nerve by advancing the plunger into the housing. At this time, the catheter is manipulated, through the catheter sheath, to bring the catheter's tip into electrical contact with the inside lumen of the needle. The anesthesia provider can operate the nerve stimulator to send a decreasing amount of electric impulse to the catheter tip, and simultaneously advance the needle tip through the patient's body towards the target nerve. After the needle tip is placed in close proximity to the target nerve, the catheter is pushed through the catheter sheath by the practitioner and advanced until the desired length of the catheter's distal end exits beyond the needle tip.

At this point, any satisfactory muscle contraction is a result of direct stimulation of the nerve by the catheter's tip and will confirm that the catheter tip has been correctly placed near the target nerve. Next, the proximal end of the catheter is released from the catheter adaptor to free the catheter, and then the needle is withdrawn while the catheter is maintained in place. Finally, the catheter adaptor is detached from the sheath's proximal hub and securely reattached to the catheter's proximal end. Care should be taken not to touch and contaminate the proximal end of the catheter and the distal part of the adaptor. At this time the catheter should be properly secured to the patient.

In an alternative method of using this embodiment, a first impulse is sent to the needle using the needle's stimulating wire. The catheter is advanced beyond the needle's distal tip, then a second impulse is sent to the catheter to verify the catheter's correct placement.

In alternative embodiments, a non-stimulating catheter is used. In non-stimulating catheter embodiments, the needle may be comprised of components that connect the needle to a supply source of electricity.

DETAILED DESCRIPTION

Figure 1:
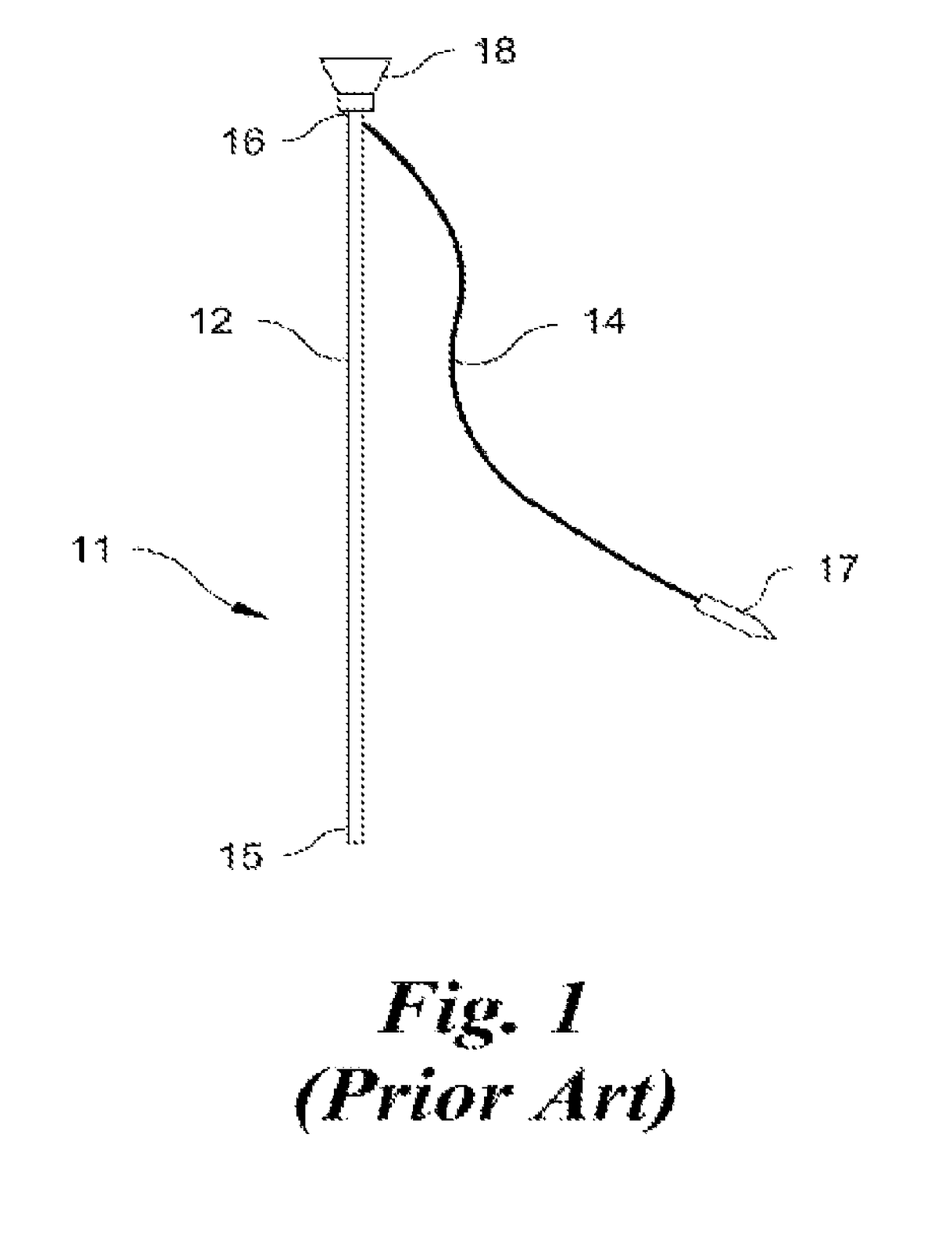
FIG. 1 is a side elevational view of a prior art needle.

Referring to FIG. 1, a conventional hollow shaft metal needle 11 is shown. These needles are well known to prior art. They are made in different lengths and gauges suitable for intended use. The needle shown in FIG. 1 has a shaft 12, a proximal end 16 and a distal tip 15. The tip 15 may be straight or beveled, or it may be made with an angle at the end of the straight shaft 12. The proximal end 16 is provided with a hub 18. The stimulator wire 14 has a first end attached to proximal end 16 and a second end adapted to connect to nerve stimulator device using connection plug 17. Using a nerve stimulator, electric impulse is sent through connection plug 17, which conveys the impulse to tip 15.

Needles, such as the one shown in FIG. 1, are usually manufactured with a shaft 12 that is covered with electrically non-conductive material on its outer surface, except along its proximal end 16 and its tip 15, which are not coated with the non-conductive material. This allows for precise placement of the tip 15 next to a nerve. A stylet (not shown) may be placed inside the shaft 12. In such an embodiment, the stylet is removed after the needle tip 15 penetrates the patient's body. Stylets are generally used to facilitate needle insertion into the patient's body and to prevent body tissues from plugging needle lumen.

Figure 2:
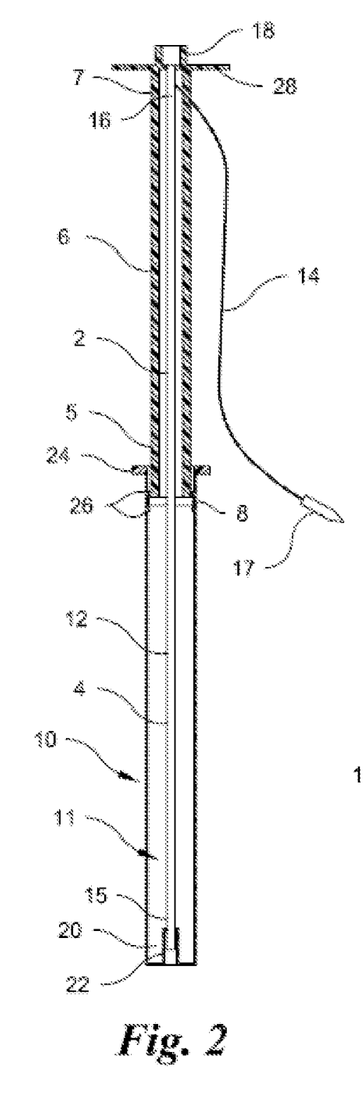
FIG. 2 is a side sectional view of a needle and plunger inside the housing according to an embodiment.
Figure 2A:
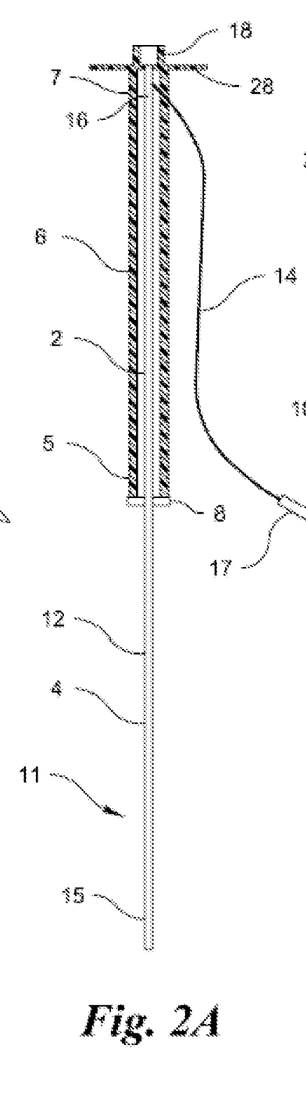
FIG. 2A is a side sectional view of a needle and plunger according to an embodiment.

Referring to FIG. 2, a hollow shaft metal needle 11 is made almost twice as long as commercially-available, similar needles. The needle 11 has a shaft 12, a proximal end 16, and a tip 15. Using standard industry methods that are well known in the art, the shaft 12 is coated with a thin layer of non-conductive material over the shaft's 12 outer surface; the tip 15 and the proximal end of the shaft 16 are not coated. The tip 15 may be straight or beveled or it may make an angle with the shaft 12. The proximal section of the needle 11 is permanently and coaxially placed inside the plunger 6. The plunger 6 has a proximal end 7, a distal annular ring 8, a thumb rest 28, and an entry hub 18. The plunger 6 divides the shaft 12 into sections 2 and 4. Section 2 is coaxially disposed within the plunger 6. The hub 18 is in fluid communication and provides access to the inside of the lumen of the needle shaft 12 and the needle tip 15.

Figure 2B:
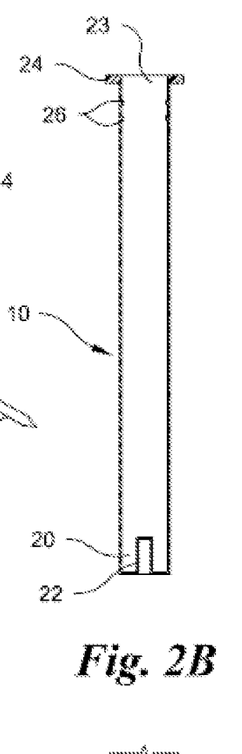
FIG. 2B is a side sectional view of a housing according to an embodiment.

The proximal end 16 may be attached to a stimulating wire 14 which is adapted to connect the needle 11 to a electric supply source. The plunger 6 is placed inside the housing 10. The housing 10 preferably has a cylindrical body. It has a distal end 20, a proximal end 23, and a distal conduit 22. The housing 10 has a length that allows the needle 11 to be withdrawn completely inside the housing 10. The inner diameter of the conduit 22 is slightly larger than the outer diameter of the needle 11, and the inner diameter of the conduit 22 will guide the needle 11 out of the distal end of the housing 10. A finger flange 24 may be attached to the proximal end 23 of the housing 10.

Figure 2C:
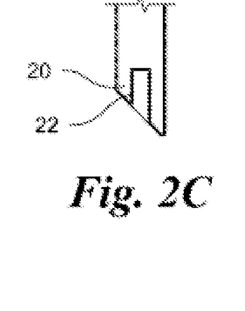
FIG. 2C is a side sectional view of a beveled distal end of a housing according to an embodiment.

Minimal friction exists between the distal annular ring 8 and the housing 10. The proximal end 23 of the housing 10 may be provided with anterior and posterior inner annular stop rings 26. These rings 26 will maintain the needle 11 completely inside the housing 10 in such a way that the needle tip 15 will rest inside the conduit 22 at a position slightly proximal to the distal end of the conduit 22. Slight force should be needed to move the annular ring 8 passed the annular stop rings 26 in either direction. The distal end 20 of the housing 10 may be beveled almost 30-45 degrees, this conforms to the angle with which the needle 11 will penetrate the patient's body. Except for the needle 12, which is preferably made of metal, the other component parts of the embodiment of the invention depicted in FIG. 2 can be made of any solid material, preferably plastic. The annular ring 8 may alternatively be made of a soft elastic material like plastic or rubber.

Marks may be placed along the plunger 6, the needle 11, or the housing 10 to help the user determine the depth of penetration of the needle 11. This could be accomplished by applying alternating colors of specific length to the outer surface of the plunger 6, the needle 11, or the housing 10, or alternatively marking lines of different thickness along the outer surface of the plunger 6, the needle 11, or the housing 10. In an alternative embodiment, the needle 11 can be attached to the distal end of the plunger 6 instead of being coaxially placed within the plunger 6. In this embodiment an axial central conduit should exist within the plunger 6 to provide fluid communication between the hub 18 and the needle 11 and to allow catheter placement into the needle 11.

Figure 9A:
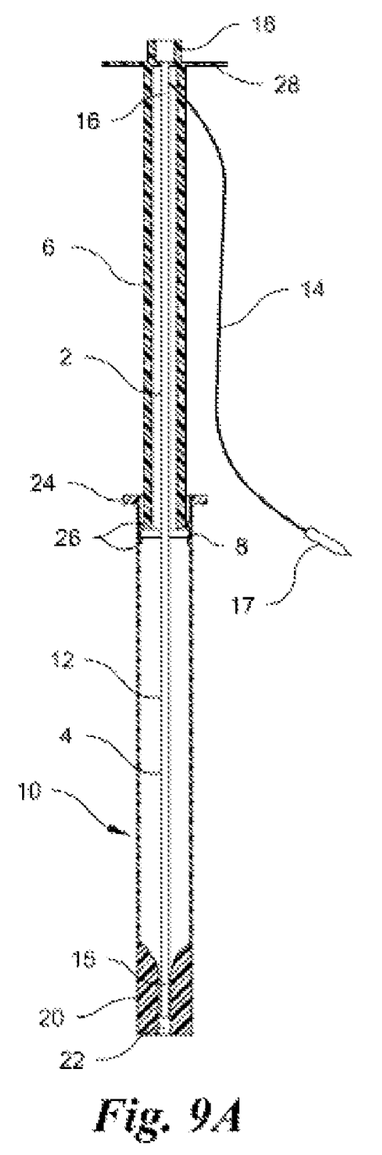
FIG. 9A is a side sectional view of one embodiment of the invention with distal conduit in the released position.
Figure 9B:
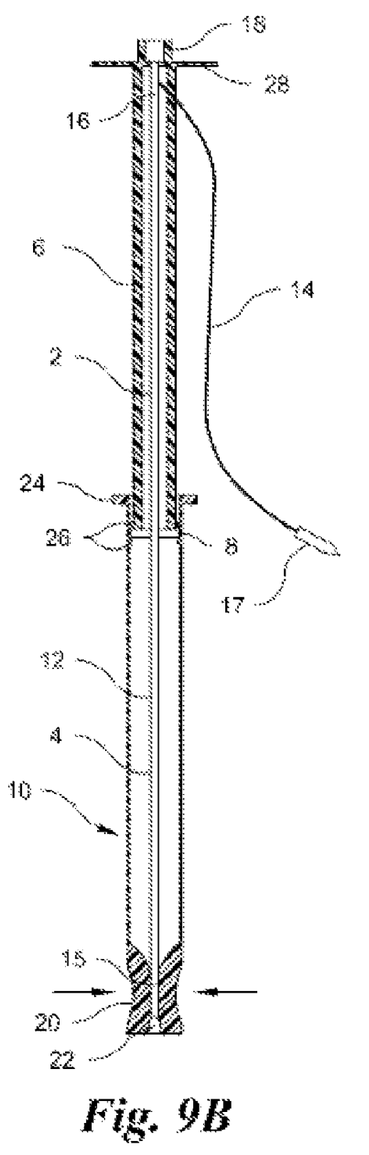
FIG. 9B is a side sectional view of one embodiment of the invention with distal conduit in the locked position.

In one embodiment of the present invention shown in FIG. 9, a catheter assembly is shown with a locking mechanism. The locking mechanism is accomplished by constructing the conduit 22 out of a soft but resilient material. The anesthesia provider can lock the needle 11 in position by simply pinching the conduit 22 between his/her fingers. Upon the release of the pressure created by the provider's fingers, the conduit 22 will resume its straight shape and free the needle 11 from its locked position. This locking mechanism may be used during the advancement of the catheter through the needle 11, so the needle 11 can be maintained in its position.

Figure 3:
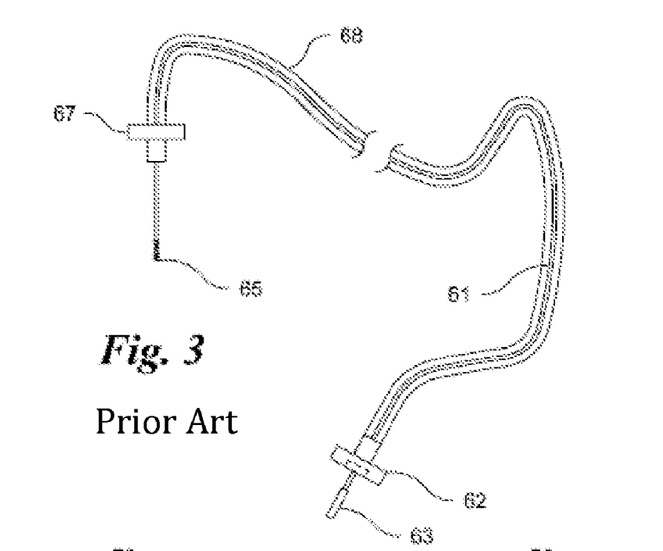
FIG. 3 is a side sectional view of a regional anesthesia catheter placed inside covering sheath according to an embodiment.

Referring to FIG. 3, a conventional stimulating regional anesthesia catheter is shown placed inside of a protective sheath. As described earlier, only the distal tip and the proximal end of the stimulating catheter are electrically exposed. The catheter has a proximal end 63, a distal tip 65, and a body 61. The catheter has means to convey electric impulse from the proximal end 63 to the distal tip 65. Any electric current sent through the proximal end 63 will only travel axially through the body 61 and exit from the distal end 65. This allows for precise placement of the catheter tip next to a target nerve. The catheter cover sheath 68 is made of thin clear plastic and is attached to the distal hub 67 and the proximal hub 62 as shown in FIG. 3. The sheath 68 is attached to periphery of hubs 67 and 62 in a sealed and secured way to maintain the sterility of the catheter 61.

Referring to FIG. 3, the sheath 68 is manufactured of adequate length as to when fully expanded, to cover the catheter 61 over its length beginning adjacent to the needle 12 and continuing until just before the proximal end 63 of the catheter 61 which is placed inside a catheter adaptor. The distal hub 67 is attached to an entry hub 18 of the plunger 6. This attachment may be permanent or, preferably releasable but secured, like a Luer fitting, or a male-female connection, or any other way known to prior art. It is important that this connection does not come apart accidentally during the catheter placement procedure, which may render the catheter 61 exposed and subject to outside contamination.

Alternatively, as explained earlier, the catheter 61 can be a non-stimulating catheter. In embodiments assembled using a non-stimulating catheter, the proximal end 63 of the catheter 61 may be maintained by a catheter adaptor attached to a proximal hub 62, or, alternatively, it may be left free inside the catheter sheath 68. This is because electrical stimulation of the catheter, during catheter placement, is not needed when a non-stimulating catheter is used. The catheter adaptor can be attached/reattached to the catheter's 61 proximal end 63 after the catheter 61 is placed correctly and the needle is removed from the patient's body.

Figure 4A:
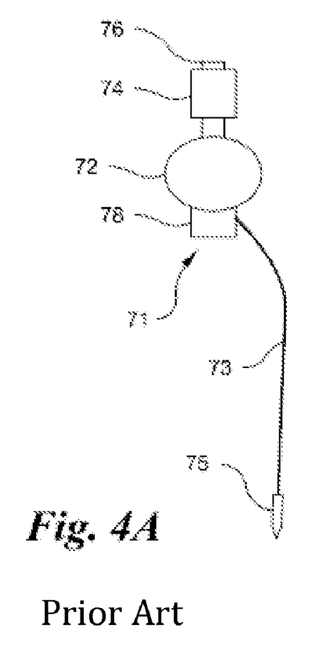
FIGS. 4A and 4B are side elevational views of a catheter adaptor according to an embodiment.
Figure 4B:
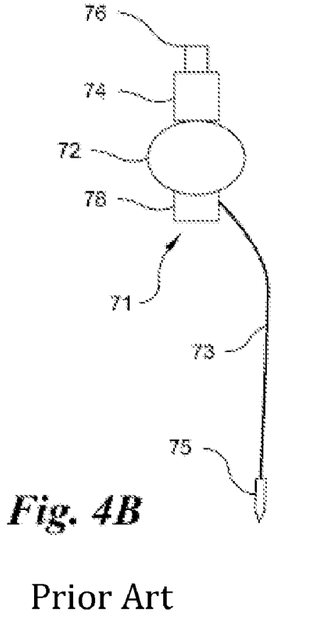

Referring to FIGS. 4A and 4B, a generic catheter adaptor 71 is shown. These adaptors generally have a first part 72 and a second part 74. The first part 72 has a front end 76 and rear end 78. The front end 76 has space in it to accept and firmly grasp the proximal end 63 of the catheter 61. This provides for an electrical connection between the catheter 61 and the catheter adaptor 71, and provides for fluid communication with the catheter 61. FIG. 4A shows the catheter adaptor 71 in the released position. In FIG. 4B, part 74 has moved in relation to part 72, which puts the catheter adaptor 71 in the locked position, which locks the proximal end 63 of the catheter in place. The rear end 78 of the catheter adaptor 71 is shaped to accept syringes of local anesthetics or infusion pumps for purposes of injecting liquid medicine through the catheter adaptor 71 into catheter lumen.

The rear end 78 of the catheter adaptor 71 is covered by a removable protective cap to maintain sterility. The catheter adaptor 71 depicted in FIGS. 4A and 4B has a stimulating wire 73 and a connecting plug 75. The connecting plug 75 is used to connect the catheter adaptor 71 to an electric supply source. The front end 76 of the adaptor 71 is connected securely, but releasably, to the proximal hub 62 of the sheath 68. This can be done, for example, with Luer fitting connections or any similar manner known to prior art. Accidental disconnection of the adaptor 71 from the proximal hub 62 during catheter placement can render the catheter 61 contaminated.

Figure 5:
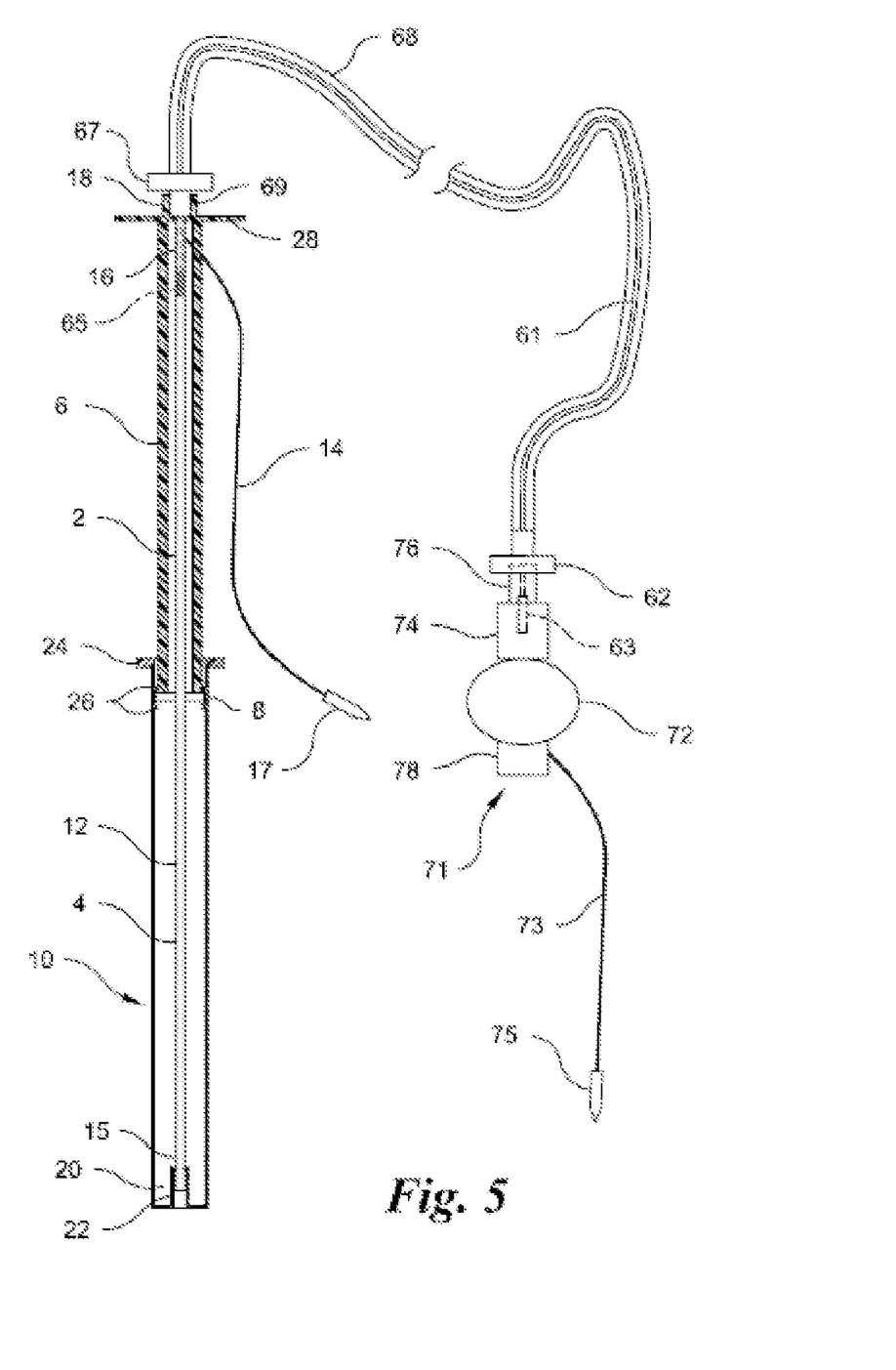
FIG. 5 is a side sectional view of a fully-assembled invention according to an embodiment.

Referring to FIG. 5, an embodiment of the catheter system is shown fully assembled. A protective cap (not shown) should cover the distal end 20. The protective cap needs to be removed just prior to needle insertion. A second cap (not shown) should cover the rear end 78 of the catheter adaptor 71. This should be removed in order to introduce local anesthetics into the catheter adaptor 71 and into the catheter lumen. As shown in FIG. 5, no areas of either the catheter or the needle are exposed.

By preloading the catheter and placing the parts of the catheter system in protective sheaths, the anesthesia provider can touch and operate the entire catheter system unit without the need to wear sterile gloves or use extensive protective draping; a simple preparation of the insertion site will suffice. A pair of clean gloves will be needed to cover the anesthesia provider's hands. The provider will join the connection plug 75 to a nerve stimulator (not shown here), then he/she will place the distal end 20 of the housing 10 against the insertion site.

Referring to FIG. 5, the needle 11 is advanced toward the targeted nerve by advancing the plunger 6 through the housing 10. Advancing the plunger 6 fully inside the housing 10 will cause the needle 11 to protrude out of the distal end 20 of the housing 10 the same length as similar commercially available needles. The anesthesia provider can operate the nerve stimulator simultaneously with the catheter system. The catheter is manipulated until its tip 65 comes in contact with the electrically conducting interior lumen of the needle 11. This will electrically couple the nerve stimulator to the needle tip 15. When the needle tip 15 is verified to be adequately close to the target nerve, the catheter 61 is grasped through the catheter sheath 68 and advanced inside the needle 11.

Marks on the catheter 61 will show the practitioner when the catheter tip 65 exits out of the needle tip 15 and loses electric contact with it. A satisfactory muscle twitch observed after this point in time is the result of direct stimulation of the target nerve by the catheter tip 65, which means correct placement of the catheter tip 65 within the nerve sheath. When an adequate length of the catheter 61 is placed adjacent to the nerve, the proximal end 63 of the catheter 61 is released from the adaptor 71. This allows the catheter end to move freely inside the sheath 68. The catheter 61 is then further fed through the plunger hub 18, while the needle 11 is simultaneously removed from the patient.

Care must be taken not to withdraw the catheter 61 while the needle 11 is being removed. When the needle tip 15 is out of the patient, the catheter 61 is held by the hand at a point distal to the needle tip 15. The proximal portion of catheter 61 is then pulled out of the sheath 68 and the needle 11. Care should be taken not to touch and contaminate the proximal end 63 of the catheter 61, and the front end 76 of the catheter adaptor 71. These two portions need to be reconnected in a sterile manner.

In some embodiments of the present invention, marks may be placed along the catheter 61 at a distance that is almost one inch away from the proximal end 63 to warn the practitioner of the eminent exit of the proximal end 63 out of the needle 11, so accidental contamination of the catheter end 63 can be avoided. The adaptor 71 at this point is released from the proximal hub 62 and reconnected to the proximal end 63. Next, the needle 11 is pulled completely into the housing 10 and is disposed of safely. Lastly, the catheter 61 is secured to the patient properly.

In an alternative embodiment, a first electric impulse is sent from a source of electricity to the needle tip 15 using the needle's stimulating wire 14. The needle tip 15 is positioned next to the nerve and the catheter 61 is then advanced, through the catheter sheath 68 and through the needle 11, to a point beyond the needle 11 tip. When the catheter 61 has been advanced to a point beyond the needle 11 tip, a second electric impulse is sent to the catheter tip 65 using the stimulating wire 73 of the catheter adaptor 71 to verify correct catheter placement. Then, the catheter proximal end 63 is freed from catheter adaptor, the needle 11 is removed, and the catheter's 61 proximal end is reattached to catheter adaptor.

In one embodiment, the invention is made the same way as described above, but instead of a stimulating catheter 61, a non-stimulating one is preloaded inside the needle 11 lumen and covered by a protective cover sheath 68. The proximal end of the catheter 61 may be grasped by a catheter adaptor, or it may be left free inside catheter sheath 68. In this embodiment, an electric impulse is sent to the needle 11 tip using the needle's 11 stimulating wire 14, the needle 11 tip is then positioned near the target nerve, and the catheter 61 is then advanced through the catheter sheath 68 and through the needle 11, to a point beyond the needle's 11 tip. The needle 11 is removed and catheter adaptor is attached/reattached to the catheter's 61 proximal end. Correct positioning of the catheter tip can be verified by visualizing the catheter tip, using an ultrasound device, or by injecting doses of local anesthetics into the catheter lumen and around the nerve and confirming the occurrence of a nerve block.

In another embodiment, the needle 11 is manufactured as a hollow shaft metal needle without insulating covering over the outside surface and without a stimulating wire 14. A non-stimulating catheter 61 is preloaded inside the needle 11 and covered with a protective sheath 68, in the same way as in other embodiments. The catheter's 61 proximal end 63 may be grasped by a catheter adaptor or it may be left free inside the catheter sheath 68.

In various embodiments, an ultrasound device may be used to visualize the target nerve and the needle 11 as the needle 11 travels through the patient's skin and into the body, and to place needle tip 15 in a position that is close to that target nerve. In embodiment described above, using ultrasound device, the needle tip 15 is placed next to a nerve, then the catheter 61 is advanced through the catheter sheath 68 and through the needle 11, and extrudes through and beyond the needle tip 15. The needle 11 is removed from the patient's body and the catheter adaptor 71 is attached/reattached to the catheter's proximal end 63. Correct positioning of the catheter tip 65 can be verified by visualizing the catheter 61 through the use of an ultrasound device, or by injecting doses of local anesthetics into the catheter lumen and around the target nerve and confirming the occurrence of a nerve block.

In an embodiment of the invention assembled using a non-stimulating catheter 61, a non-stimulating catheter adaptor 71 may be used. While a stimulating catheter adaptor 71 is comprised of components that allow a nerve stimulator device to be connected to the catheter's proximal end 63 to send electrical impulses to the catheter 61, a non-stimulating catheter adaptor 71 is devoid of such components. However, similar to a stimulating catheter 61, a non-stimulating catheter 61 will tightly grasp the catheter's proximal end 63 and provide for fluid access into the catheter lumen.

In other embodiments, one or more orifices may be provided along the section 2 of the needle 11. Space should exist between this portion of the needle 11 and the interior lumen of the plunger 6. The plunger 6 should be made of clear plastic. In this embodiment, if accidental intravascular entry happens, blood will enter into the open space inside the plunger 6 and can be seen by the anesthesia provider. Exit holes may be placed, preferably on the proximal end of the plunger 6, to allow air to exit as blood flows in. In this embodiment, it is necessary that the catheter tip 65 be placed proximal to the orifices so as not to block the flow of blood if intravascular entry happens.

Figure 6:
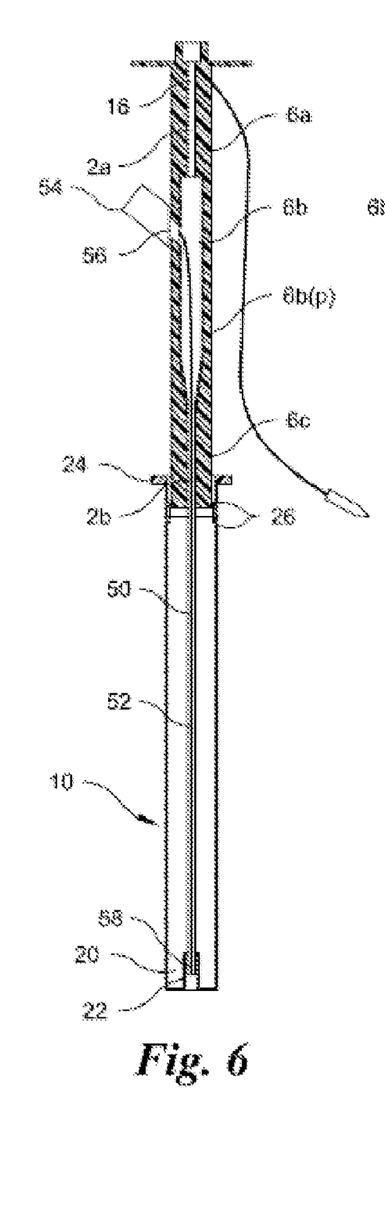
FIG. 6 is a side sectional view of one embodiment of the invention having a stylet placed inside needle.

In the embodiment depicted in FIG. 6, the invention may include a stylet 50. A stylet 50 is comprised of an elongated body made of metal or preferably plastic. The stylet 50 may be removably placed inside a hollow needle. Stylets are designed to facilitate insertion of a needle into a patient's body and also prevent skin or other tissue materials from plugging the needle's relatively large bore. In FIG. 6, the plunger 6 is comprised of a proximal portion 6a, a middle portion 6b, and a distal portion 6c. The section 2 of the needle 11 also has a proximal portion 2a and a distal portion 2b.

Figures 6A, 6B:
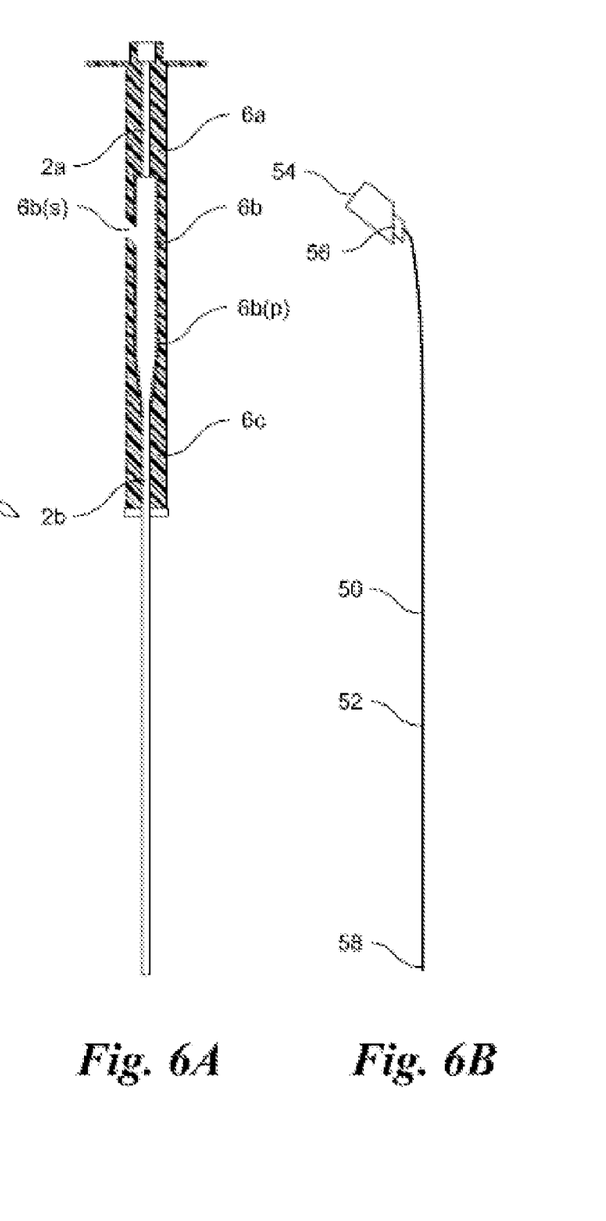
FIG. 6A is a side sectional view of a plunger and needle, with the plunger having a side slot for insertion of the stylet, according to an embodiment.
FIG. 6B is a side sectional view of a stylet according to one embodiment of the invention.

Needle portions 2a and 2b are connected by a metal plate 6b(p), which runs through the middle portion 6b of the plunger 6. The middle portion 6b of the plunger 6 is an enlarged space that is in fluid communication with needle portions 2a and 2b. The middle portion 6b of the plunger 6 not only allows for the insertion or withdrawal of the stylet 50, it will also allow blood to freely flow into the plunger 6 in case the needle 11 accidentally pierces a vein or artery when the stylet 50 is removed. The internal diameters of portions 2a and 2b are the same as the internal diameter of the entire needle 11. The needle 11 again is electrically insulated on its outer surface, except its tip 15 and proximal end 16. The proximal end 16 may be connected to a stimulating wire 14.

Any electric current coming through needle portion 2a, either through the wire 14 or by way of contact with the catheter tip 65, will exit only from the tip 15. The middle portion 6b of the plunger 6 also has a slot 6b(s). This slot 6b(s) is designed to allow insertion of the stylet 50. FIG. 6B depicts a stylet 50 designed to fit the embodiment shown in FIG. 6. It has a body 52, a tip 58 and a knob 54 and a plug 56. The stylet 50 can be inserted and withdrawn through slot 6b(s) of the middle portion 6b. The plug 56 is sized to fit snugly into slot 6b(s) and the knob 54 can be grabbed by the practitioner so the stylet 50 can be inserted or withdrawn. When fully advanced, the stylet tip 58 will reach the needle tip 15 and will be flush with the needle tip 15.

Figure 7:
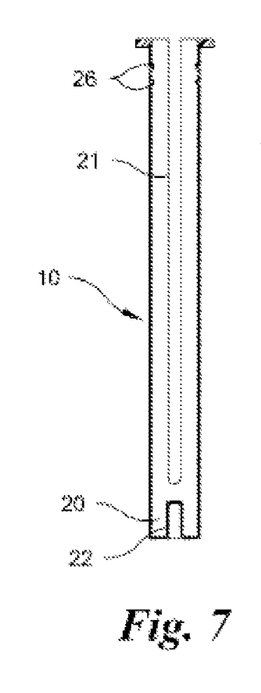
FIG. 7 is a side sectional view of one embodiment of the housing with side longitudinal slot.
Figures 7A, 7B:
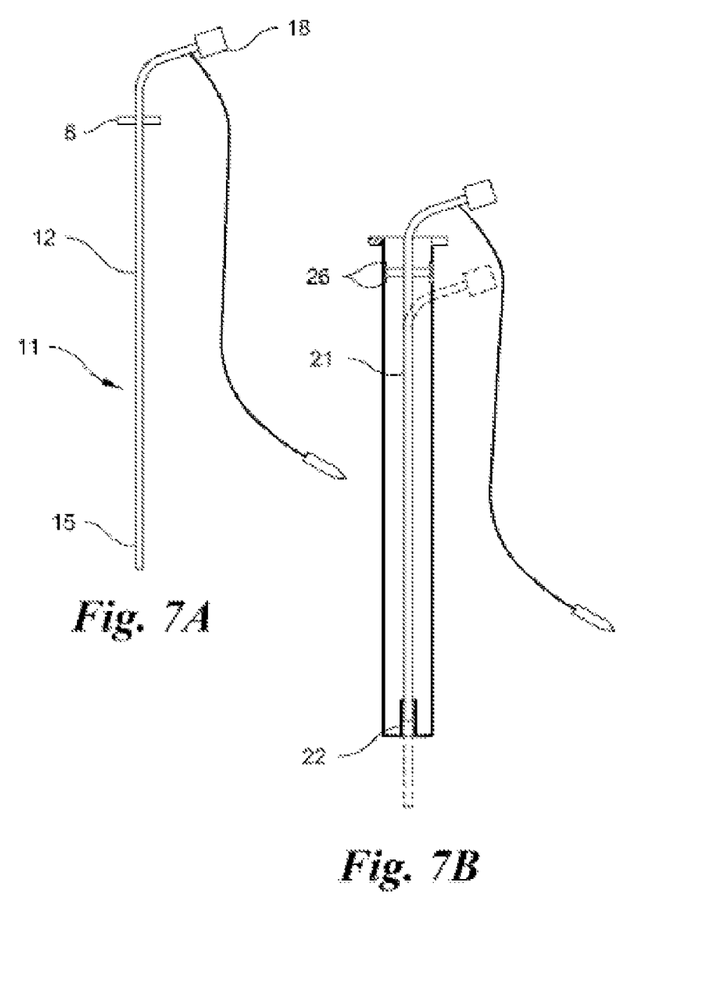
FIG. 7A is a side sectional view of one embodiment of the needle with curved proximal end.
FIG. 7B is a side sectional view of one embodiment of the invention with the needle placed inside the housing and with the curved proximal end of the needle placed inside side slot.

In one embodiment shown in FIGS. 7 through 7B, the housing 10 is provided with a longitudinal side slot 21. The side slot 21 runs on the side of the housing 10, from the proximal end 23 to just above the conduit 22. It is sized to fit the needle 11. In this embodiment, the proximal end 23 of the needle 11 is curved and faces outward as is shown in FIG. 7A. This curve allows the needle hub 18 to maintain its position just next to and out of the housing 10. This positioning allows the practitioner to grab the hub 18 in order to advance the needle 11 through the housing 10 by way of sliding the needle alongside the slot 21. An annular ring 8 is placed around needle 11 at a place between the curved and straight portions of the needle 11. As in the other embodiment of the invention shown in FIG. 5, the catheter 61 is preloaded inside needle 11 and is covered with the sheath 68. The distal hub 67 is attached to the hub 18 as it is in other embodiments of the invention. As can be seen in FIG. 7B, by providing a slot 21, the needle 11 and the catheter system can be made much shorter than other embodiments without sacrificing the actual needle length available to penetrate the patient's body.

Figure 8:
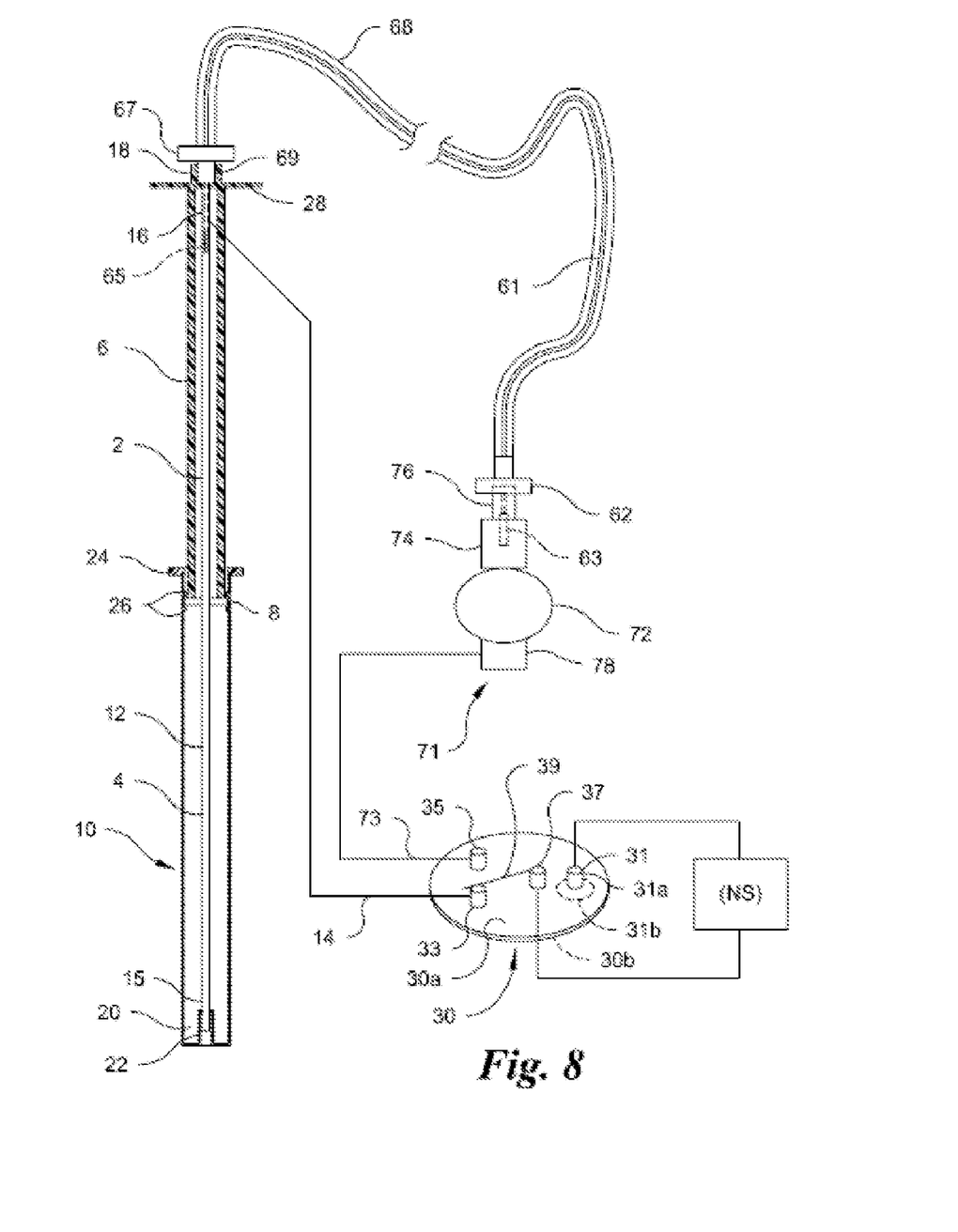
FIG. 8 is a side sectional view of one embodiment of the invention fully assembled with schematic depiction of switch pad and nerve stimulator device (NS).

In an alternative embodiment shown in FIG. 8, the invention comprises a switch pad 30. While the switch pad 30 can be any size and shape, the switch pad 30 is preferably similar in size, shape and structure to a regular ECG pad. An electric impulse is sent to the needle 11 by way of contact with catheter tip 65. Alternatively, the needle 11 can be connected to the nerve stimulator directly using a needle wire 14 and then the catheter is connected to the nerve stimulator by disconnecting the nerve stimulator from the needle and attaching it to catheter 61 through the catheter adaptor 71.

The switch pad 30 allows the task of electrically stimulating the needle 11 and/or the catheter 61 quickly and/or single-handedly. The switch pad 30 is made of soft plastic or a similar non-conductive material. The switch pad 30 has a top surface 30a and a bottom surface 30b. The bottom surface 30b is covered with a layer of adhesive material which enables the switch pad 30 to be temporarily attached to the patient's body. A knob 31 is affixed into the switch pad 30. The knob 31 is constructed of a conductive material. The knob 31 has a cylindrical top portion 31a and a disc-shaped bottom portion 31b. The knob 31 is positioned into the switch pad 30 in such a way that the cylindrical top portion 31a sits perpendicularly on the top surface 30a while the disc-shaped bottom portion 31b is attached to and is substantially flush with the bottom surface 30b of the switch pad 30. The 31b portion is covered with a layer of conductive gel to facilitate its electric connection to the patient's body.

Attaching the switch pad 30 to a patient's body will provide an electrical connection between the patient's skin and the knob 31. The knob 31 will function as a ground connection between the patient body and a nerve stimulator device. The switch pad 30 is further comprised of knobs 33 and 35. These knobs 33, 35 are made of conductive material, but they are electrically isolated in such way that no connection exits between the two knobs 33, 35, or between the two knobs 33, 35 and the bottom surface 30b.

The stimulating wire 14 of the needle 11 and the wire 73 of the catheter adaptor 71 can be attached to the knobs 33, 35 using standard alligator clips. As is shown in FIG. 8, a metal pivot 37 is provided on the top surface 30a. A metal bar 39 is attached to the pivot 37 in such a way that it can move between the two knobs 33, 35. The metal bar 39 maintains a constant electrical connection to the pivot 37. A dent or slot may be provided on the side of knobs 33, 35 to hold the metal bar 39 snugly in position in order to provide a reliable electrical connection. As is shown in FIG. 8, wires from the nerve stimulator can be connected to the knob 31 and the pivot 37 using alligator clips.

Referring to FIG. 8, at the beginning of the catheter placement procedure, wires 14 and 73 are connected to knobs 33 and 35. The needle 11 is electrically stimulated. Thereafter, when the catheter 61 is advanced through the needle 11 and placed into position near the target nerve, the anesthesia provider can then switch to catheter stimulation by moving the metal bar 39 from its position against knob 33 to a position against knob 35. Alternatively, the switch pad 30 may only have knob 37 and knob 31. Knob 31 provides a grounding connection. The second wire of the nerve stimulator is attached to the knob 37 using an alligator clip. Then the anesthesia provider can switch from needle stimulation to catheter stimulation and vise versa by attaching wires 14 and 73 to the knob 37 in an alternating fashion.

Other embodiments of the invention comprise a sealing diaphragm around catheter 61. The sealing diaphragm may be needed if the anesthesia provider wishes to inject liquids like normal saline into the catheter 61, before the catheter 61 is advanced through the needle 11, to facilitate catheter 61 advancement within the nerve sheath. In this embodiment, a sealing diaphragm may be provided around the catheter 61 at the level of the hub 67 or the hub 18. The function of the sealing diaphragm is to prevent liquid from flowing back inside the sheath 68. The catheter tip is advanced to the position of the needle tip 15, then liquid is injected into catheter 61 through catheter adaptor to exit from catheter tip and be deposited in the nerve sheath.

I claim:

1. A medical device for the placement of regional anesthesia catheters, said device comprising:
    (a) a hollow needle comprising a shaft, a proximal end and a distal tip;
    (b) a plunger attached to or around said proximal end of said needle, said plunger comprising a hub, said hub providing access to the interior lumen of said needle;
    (c) a housing having a proximal end and a distal end, said housing being dimensioned to allow said plunger to move inside of said housing with friction;
    (d) a regional anesthesia catheter comprising a hollow body, a proximal end and a distal tip, said distal tip being pre-loaded inside said needle; and
    (e) a clear, flexible sheath comprising a proximal hub and a distal hub, said distal hub being attached to said hub of said plunger, and said sheath covering said catheter.

2. The medical device of claim 1, further comprising a catheter adaptor, wherein said catheter adaptor is attached to said proximal hub of said sheath.

3. The medical device of claim 2, wherein said catheter adaptor comprises a means for conveying an electric impulse from an electric supply source to said proximal end of said catheter.

4. The medical device of claim 1, wherein said catheter further comprises a means for conveying an electric impulse from said proximal end of said catheter to said distal tip of said catheter.

5. The medical device of claim 4, wherein said catheter tip is in contact with the interior lumen of said needle such that an electric current sent through said catheter is conveyed to said needle's distal tip.

6. The medical device of claim 1, wherein said needle is able to convey electric impulses from said proximal end of said needle to said distal tip of said needle, and said needle further comprising an outer surface that is covered with an insulating material.

7. The medical device of claim 6, wherein said needle further comprises a stimulating wire, said wire comprising a first end attached to said proximal end of said needle and a second end adapted to connect to an electric supply source.

8. The medical device of claim 1, wherein said housing further comprises a conduit at said distal end of said housing, said conduit being dimensioned in such a way as to guide said needle out of said housing.

9. The medical device of claim 8, wherein said conduit is made of a flexible material such that compressing said conduit will lock said needle into position and releasing compression will free said needle from its locked position.

10. The medical device of claim 1, wherein said distal end of said housing is beveled.

11. The medical device of claim 1, wherein said catheter comprises marking to show the position of said catheter in relation to said needle.

12. The medical device of claim 1, further comprising a sealing diaphragm positioned around said catheter at a point distal to said distal end of said sheath.

13. The medical device of claim 1, wherein said needle comprises at least one orifice on said shaft of said needle for allowing the visible flow of blood out of said needle.

14. The medical device of claim 1, further comprising a plurality of markings that show the depth of penetration of said needle into a patient's body.

15. The medical device of claim 1, further comprising a stylet.

16. The medical device of claim 1, further comprising a switch pad, said switch pad comprising a top surface and a bottom surface, said bottom surface being covered with layer of adhesive material, said switch pad further comprising at least two knobs for connecting to an electric supply source, one of said knobs being able to contact with a patient's body and providing for ground connection between the patient's body and said electric supply source, said switch pad further comprising a means for connecting said electric supply source to said needle through said needle's stimulating wire and to said catheter through said catheter adaptor.

17. A medical device for the placement of regional anesthesia catheters, said device comprising:
 (a) a hollow needle comprising a straight shaft, a curved proximal end, a proximal hub, and a distal tip;
 (b) an annular ring placed around said needle;
 (c) a housing comprising a proximal end, a distal end, and a side longitudinal slot, said slot being sized to fit said curved portion of said needle, said housing dimensioned to allow said annular ring to move inside said housing with friction, said needle placed inside said housing with said curved portion placed inside said slot;
 (d) a regional anesthesia catheter comprising a hollow body, a proximal end and a distal tip, said distal tip being pre-loaded inside said needle; and
 (e) a clear, flexible sheath comprising a proximal hub and a distal hub, said distal hub being attached to said proximal hub of said needle, and said sheath covering said catheter.

18. The medical device of claim 17, further comprising a catheter adaptor, wherein said catheter adaptor is attached to said proximal hub of said sheath.

19. The medical device of claim 17, wherein said catheter adaptor comprises a means for conveying an electric impulse from an electric supply source to said proximal end of said catheter.

20. The medical device of claim 17, wherein said catheter further comprises a means for conveying an electric impulse from said proximal end of said catheter to said distal tip of said catheter.

21. The medical device of claim 20, wherein said catheter tip is in contact with the interior lumen of said needle such that an electric current sent through said catheter is conveyed to said needle's distal tip.

22. The medical device of claim 17, wherein said needle is able to convey electric impulses from said proximal end of said needle to said distal tip of said needle, and said needle further comprising an outer surface that is covered with an insulating material.

23. The medical device of claim 22, wherein said needle further comprises a stimulating wire, said wire comprising a first end attached to said proximal end of said needle and a second end adapted to connect to an electric supply source.

24. The medical device of claim 17, wherein said housing further comprises a conduit at said distal end of said housing, said conduit being dimensioned in such a way as to guide said needle out of said housing.

25. The medical device of claim 24, wherein said conduit is made of a flexible material such that compressing said conduit will lock said needle into position and releasing compression will free said needle from its locked position.

26. The medical device of claim 17, wherein said distal end of said housing is beveled.

27. The medical device of claim 17, wherein said catheter comprises marking to show the position of said catheter in relation to said needle.

28. The medical device of claim 17, further comprising a sealing diaphragm positioned around said catheter at a point distal to said distal end of said sheath.

29. The medical device of claim 17, wherein said needle comprises at least one orifice on said shaft of said needle for allowing the visible flow of blood out of said needle.

30. The medical device of claim 17, further comprising a plurality of markings that show the depth of penetration of said needle into a patient's body.

31. The medical device of claim 17, further comprising a switch pad, said switch pad comprising a top surface and a bottom surface, said bottom surface being covered with layer of adhesive material, said switch pad further comprising at least two knobs for connecting to an electric supply source, one of said knobs being able to contact with a patient's body and providing for ground connection between the patient's body and said electric supply source, said switch pad further comprising a means for connecting said electric supply source to said needle through said needle's stimulating wire and to said catheter through said catheter adaptor.

* * * * *